US010532092B2

United States Patent
Guo et al.

(10) Patent No.: US 10,532,092 B2
(45) Date of Patent: Jan. 14, 2020

(54) MINERALIZED FOOT-AND-MOUTH DISEASE VIRUS LIKE PARTICLES, AND PREPARATION METHOD AND USE THEREOF

(71) Applicants: Lanzhou Veterinary Research Institute Chinese Academy of Agricultural Sciences, Lanzhou (CN); Zhejiang University, Hangzhou (CN)

(72) Inventors: Huichen Guo, Lanzhou (CN); Shiqi Sun, Lanzhou (CN); Ping Du, Lanzhou (CN); Zhidong Teng, Lanzhou (CN); Ruikang Tang, Lanzhou (CN); Ruibo Zhao, Lanzhou (CN); Jiaxi Ru, Lanzhou (CN); Yanquan Wei, Lanzhou (CN); Yun Zhang, Lanzhou (CN); Yuan Gao, Lanzhou (CN); Junwu Ma, Lanzhou (CN); Xiangtao Liu, Lanzhou (CN); Hong Yin, Lanzhou (CN)

(73) Assignees: LANZHOU VETERINARY RESEARCH INSTITUTE CHINESE ACADEMY OF AGRICULTURAL SCIENCES, Lanzhou (CN); ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 16/027,289

(22) Filed: Jul. 4, 2018

(65) Prior Publication Data

US 2019/0008944 A1 Jan. 10, 2019

(30) Foreign Application Priority Data

Jul. 4, 2017 (CN) .......................... 2017 1 0539048

(51) Int. Cl.
*A61K 39/12* (2006.01)
*A61K 39/00* (2006.01)

(52) U.S. Cl.
CPC ...... *A61K 39/12* (2013.01); *A61K 2039/5258* (2013.01); *C12N 2770/32123* (2013.01); *C12N 2770/32134* (2013.01)

(58) Field of Classification Search
CPC ............ A61K 39/12; A61K 2039/5258; A61K 39/135; A61K 2039/552; A61K 39/00; A61K 2039/555; A61K 2039/5254; A61K 2039/6075; A61K 2039/525; A61K 39/125; A61K 47/6889; A61K 47/6901; C12N 7/00; C12N 2770/32122; C12N 2770/32134; C12N 2770/32123; C12N 15/86; C12N 2770/32151; C12N 9/506; C12N 15/8258; C12N 2500/05; C12N 2500/10; C12N 15/70; C07K 14/005; C07K 16/1009; C07K 2319/00; C07K 7/08
See application file for complete search history.

(56) References Cited

PUBLICATIONS

Wang G, Cao RY, Chen R, Mo L, Han JF, Wang X, Xu X, Jiang T, Deng YQ, Lyu K, Zhu SY, Qin ED, Tang R, Qin CF. Rational design of thermostable vaccines by engineered peptide-induced virus self-biomineralization under physiological conditions. Proc Natl Acad Sci U S A. May 7, 2013;110(19):7619-24. Epub Apr. 15, 2013.*
Yan D, Teng Z, Sun S, Jiang S, Dong H, Gao Y, Wei Y, Qin W, Liu X, Yin H, Guo H. Foot-and-mouth disease virus-like particles as integrin-based drug delivery system achieve targeting anti-tumor efficacy. Nanomedicine. Apr. 2013;13(3):1061-1070. Epub Dec. 18, 2016.*
P. Du, R. Liu, S.Sun, H. Dong, R. Zhao, R. Tang, J. Dai, H. Yin, J. Luo, Z. Liu and H. Guo, Nanoscale, 2019, DOI: 10.1039/C9NR05549E.*

\* cited by examiner

*Primary Examiner* — Rachel B Gill
(74) *Attorney, Agent, or Firm* — Matthias Scholl P.C.; Matthias Scholl

(57) ABSTRACT

Foot-and-mouth disease virus like particles, the particles including a structural protein VP0, a structural protein VP1 including a mineralization peptide, a structural protein VP3, and a calcium phosphate coat. The structural protein VP1 including a mineralization peptide is encoded by a gene sequence represented by SEQ ID NO. 7, SEQ ID NO. 8 or SEQ ID NO. 9. The structural protein VP0 is encoded by a gene sequence represented by SEQ ID NO. 2. The structural protein VP3 is encoded by a gene sequence represented by SEQ ID NO. 3. The calcium phosphate coat covers the structural protein VP0, the structural protein VP1 including a mineralization peptide, and the structural protein VP3.

6 Claims, 14 Drawing Sheets

Specification includes a Sequence Listing.

FIG. 10

MINERALIZED FOOT-AND-MOUTH DISEASE VIRUS LIKE PARTICLES, AND PREPARATION METHOD AND USE THEREOF

CROSS-REFERENCE TO RELAYED APPLICATIONS

Pursuant to 35 U.S.C. § 119 and the Paris Convention Treaty, this application claims foreign priority to Chinese Patent Application No. 201710539048.3 filed Jul. 4, 2017, the contents of which and any intervening amendments thereto are incorporated herein by reference. Inquiries from the public to applicants or assignees concerning this document or the related applications should be directed to: Matthias Scholl PC., Attn.: Dr. Matthias Scholl Esq., 245 First Street, 18th Floor, and Cambridge, Mass. 02142.

BACKGROUND

The disclosure relates to foot-and-mouth disease virus like particles, a method for preparing the same, and also use of the foot-and-mouth disease virus like particles in the prevention and treatment of foot-and-mouth disease.

Foot-and-mouth disease (FMD) is an infectious and sometimes fatal viral disease that affects cloven-hoofed animals, including domestic and wild bovids.

Virus-like particles (VLPs) resemble viruses, but are non-infectious because they contain no viral genetic material. VLPs are widely used in the development of human and veterinary vaccines.

Conventional VLPs are susceptible to temperature.

SUMMARY

The disclosure provides foot-and-mouth disease virus like particles that are insusceptible to temperature, as well as a method for preparing the same.

Disclosed are foot-and-mouth disease virus like particles, the particles comprising a structural protein VP0, a structural protein VP1 comprising a mineralization peptide, a structural protein VP3, and a calcium phosphate coat. The structural protein VP1 comprising a mineralization peptide is encoded by a gene sequence represented by SEQ ID NO. 7, SEQ ID NO. 8 or SEQ ID NO. 9; the structural protein VP0 is encoded by a gene sequence represented by SEQ ID NO. 2; the structural protein VP3 is encoded by a gene sequence represented by SEQ ID NO. 3; and the calcium phosphate coat covers the structural protein VP0, the structural protein VP1 comprising a mineralization peptide, and the structural protein VP3.

The structural protein VP1 comprising a mineralization peptide can be encoded by the gene sequence represented by SEQ ID NO. 9.

The mineralization peptide of the structural protein VP1 can be encoded by a gene sequence represented by SEQ ID NO. 4, SEQ ID NO. 5 or SEQ ID NO. 6.

The disclosure further provides a method for preparing foot-and-mouth disease virus like particles, the method comprising:

(1) constructing a recombinant plasmid comprising genes encoding a structural protein VP0, a structural protein VP1 comprising a mineralization peptide, and a structural protein VP3 of foot-and-mouth disease virus (FMDV), wherein: the structural protein VP1 comprising a mineralization peptide is encoded by a gene sequence represented by SEQ ID NO. 7, SEQ ID NO. 8 or SEQ ID NO. 9; the structural protein VP0 is encoded by a gene sequence represented by SEQ ID NO. 2; the structural protein VP3 is encoded by a gene sequence represented by SEQ ID NO. 3;

(2) expressing and purifying the structural protein VP0, the structural protein VP1 comprising a mineralization peptide, and the structural protein VP3 of FMDV;

(3) assembling FMD VLPs; and (4) mineralizing the FMD VLPs.

The method for preparing foot-and-mouth disease virus like particles comprises:

a). employing genomic DNA of *Saccharomyces cerevisiae* as a template and using smt3F and smt3R as primers, amplifying a smt3 gene, where the gene sequences of the primers are as follows:

```
smt3F:
                                    (SEQ ID NO. 10)
5'GCCATGGGTCATCACCATCATCATCACGGGTCGGACTCAGAAGTCAAT
CAA3';

smt3R:
                                    (SEQ ID NO. 11)
5'GGATCCGAGACCTTAAGGTCTCAACCTCCAATCTGTTCGCGGTG 3';
``` b). digesting the smt3 gene and a vector pET-28a using restriction enzymes Nco I and BamH I, inserting the digested smt3 gene into the digested pET-28a vector, to yield a vector pSMK; and replacing a kanamycin resistance gene of the vector pSMK by an ampicillin resistance gene, to yield a vector pSMA;

c). synthesizing coding genes of structural proteins VP0, VP3, and VP1 according to the gene sequence of serotype 0 FMD virus, where the coding gene of the structural protein VP1 is represented by SEQ ID NO. 1, the coding gene of the structural protein VP0 is represented by SEQ ID NO. 2, and the coding gene of the structural protein VP3 is represented by SEQ ID NO. 3; employing the synthesized coding genes of structural proteins VP0, VP3, and VP1 as templates, employing VP1F/VP1R, VP0F/VP0R, and VP3F/VP3R as primers, and amplifying the coding genes of the structural proteins VP0, VP3, and VP1, respectively; where the gene sequences of the primers are as follows:

```
VP1F:
                                    (SEQ ID NO. 12)
5'GGTCTCTAGGTACCACCAGCACGGGCGAA 3'

VP1R:
                                    (SEQ ID NO. 13)
5'-CGCGGATCCTCACAGACTTTGTTTGACCGG 3'

VP0F:
                                    (SEQ ID NO. 14)
5'GGTCTCTAGGTGGTGCGGGCCAGTCATCTCC 3'

VP0R:
                                    (SEQ ID NO. 15)
5'CGCGGATCCTCATTCTTTACTCGGAAATTC 3'

VP3F:
                                    (SEQ ID NO. 16)
5'GGTCTCTAGGT GGTATCTTCCCGGTGGCGTG 3'

VP3R:
                                    (SEQ ID NO. 17)
5'CGCGGATCCTCA TTGCTGACGGGCATCAACC 3'
``` d). digesting the amplified coding genes of the structural proteins VP0, VP3, and VP1 using the restriction enzymes BsmBI/BamH I, digesting the vector pSMK and pSMA using the restriction enzyme BsaI, inserting the digested coding genes of the structural proteins VP0, VP3, and VP1 into the digested pSMK or pSMA, to yield recombinant expression vectors pSMK/VP0, pSMK/VP1, and pSMA/VP3, respectively;

e). employing the recombinant expression vector pSMK/VP1 as a template, employing T7BamHI/VP1XhoI as primers, and amplifying a DNA fragment comprising T7 promoter and the coding gene of the structural protein VP1; digesting the DNA fragment and the recombinant expression vector pSMK/VP0 using restriction enzymes BamHI/XhoI, to yield a recombinant co-expression vector pSMK/VP0-VP1, where gene sequences of the primers T7BamHI/VP1XhoI are as follows:

```
T7BamHI:
                                   (SEQ ID NO. 18)
5'GCAATTGGATCCCGTCCGGCGTAGAGGATCGA 3'

VP1XhoI:
                                   (SEQ ID NO. 19)
5'GCGCACCTCGAGTCACAGAGTCTGTTTCTCAGG 3'
``` f). providing a mineralization peptide represented by SEQ ID NO. 4, SEQ ID NO. 5, or SEQ ID NO. 6, employing the recombinant co-expression vector pSMK/VP0-VP1 as a template, inserting the gene sequence of the mineralization peptide into a gene point of the VP1 gene sequence corresponding to the $150^{th}$ amino acid of the structural protein VP1 using inverse PCR (polymerase chain reaction), to yield a VP1 recombinant plasmid comprising the gene sequence of the mineralization peptide, which is represented by SEQ ID NO. 7, SEQ ID NO. 8, or SEQ ID NO. 9;

g). co-transforming the recombinant plasmid comprising the gene sequence of the mineralization peptide and the vector pSMA/VP3 into an expression strain BL21(DE3), inoculating the expression strain onto a culture plate containing kanamycin, chloromycetin, and ampicillinum, incubating overnight, screening out and scale-up culturing positive clones containing the mineralization peptide, purifying the positive clones, to yield target proteins;

h). digesting the target proteins using a ubiquitin protease, removing ubiquitin-modified proteins using HisTrap HP chromatography, collecting and putting a flow-through liquid containing the structural proteins VP0, VP1, and VP3 into a pH 8.0 buffer solution containing 20 mM Tris-HCl and 500 mM NaCl, and allowing the buffer solution to stand at 4° C. overnight, to yield VLPs; and i). adding the VLPs to a first solution with pH 7.4 and comprising 80-100 mM $Na^+$, 1-10 mM $K^+$, 1-5 mM $Ca^{2+}$, 1-10 mM $Mg^{2+}$, 100-200 mM $Cl^-$, 10-20 mM $HCO_3^-$, 1-10 mM $HPO_4^{2-}$, and 1-10 mM $PO_4^{3-}$, and incubating for 10 min at room temperature; adding a second solution, pH 7.4 and equal to the first solution in volume, comprising 80-150 mM $Na^-$, 2-20 mM $Mg^{2+}$, 1-20 mM $Ca^{2+}$, 100-200 mM $Cl^-$, 100-200 mM $HCO_3^-$, 1-10 mM $HPO_4^{2-}$, and 1-10 mM $PO_4^{3-}$ to the first solution, incubating at 4° C. overnight, and centrifuging for 10 min at 16000 rpm.

The structural protein VP1 comprising a mineralization peptide can be encoded by SEQ ID NO. 9.

The disclosure also provides a method of preparing a foot-and-mouth disease vaccine, the method comprising applying the foot-and-mouth disease (FMD) virus like particles (VLPs).

The foot-and-mouth disease vaccine can be prepared and stored at normal temperature.

Advantages of the foot-and-mouth disease (FMD) virus like particles (VLPs) of the disclosure are summarized as follows.

In the disclosure, the principle of biomineralization is employed to develop a heat-resistant vaccine, by inserting a mineralization peptide into the VP1 protein of the FMD virus, to obtain VLPs coated with a mineralized layer that can bind to calcium ions. The prepared FMD VLPs are insusceptible to the temperature, which is conducive to the development of normal temperature vaccines.

BRIEF DESCRIPTION OF THE DRAWINGS

FIG. 10 shows changes in antibody levels in guinea pigs immunized with various VLPs.

DETAILED DESCRIPTION

Figure 1:
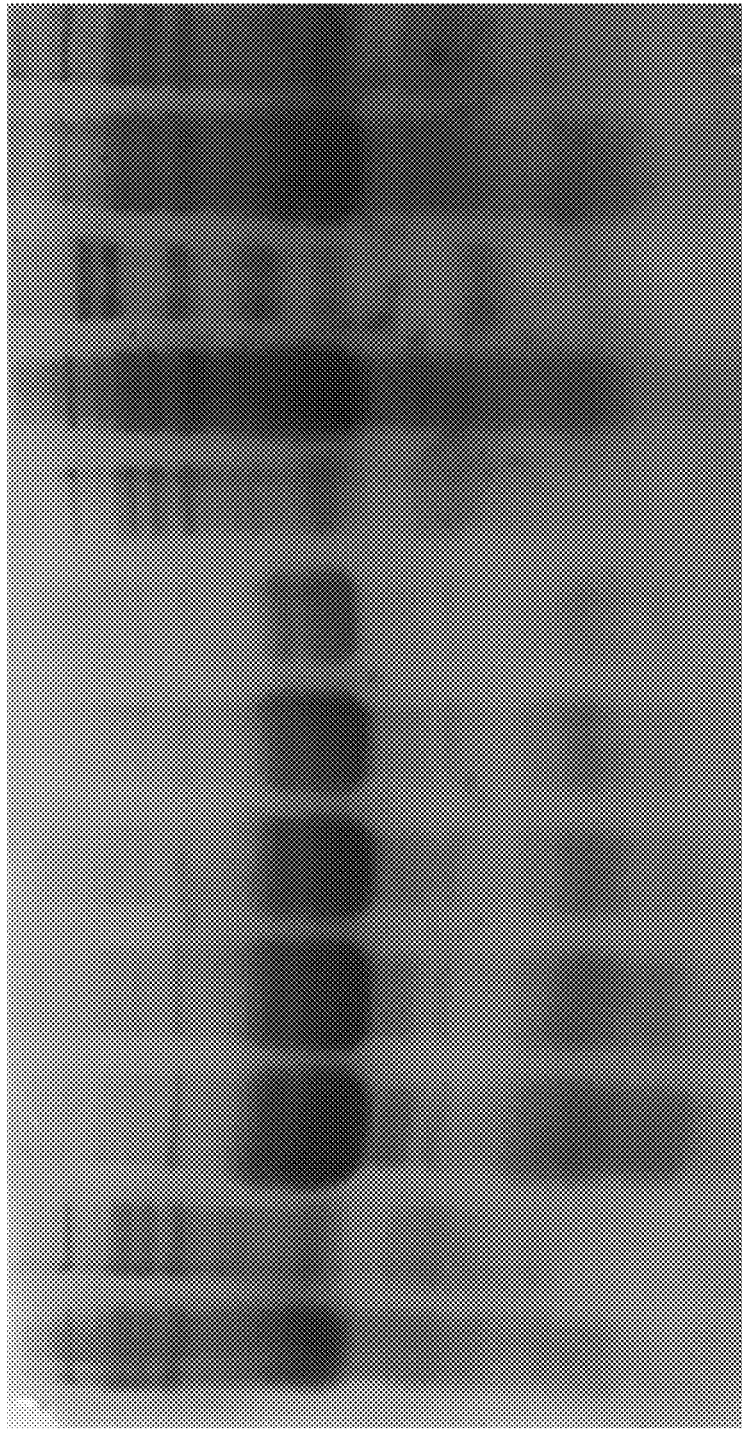
FIG. 1 shows the induced expression and purification of fusion proteins containing different mineralization peptides;
 1. N6VP1/VP3, after being induced; 2. N6VP1/VP3, before being induced; 3-4. purified N6VP1/VP3 sample; 5-6. purified W6 VP1/VP3 sample; 7. purified NwVP1/VP3 sample; 8. W6 VP1/VP3, before being induced; 9. W6 VP1/VP3, after being induced; 10. Marker; 11. NwVP1/VP3, after being induced; 12. NwVP1/VP3, before being induced.
Figure 2:
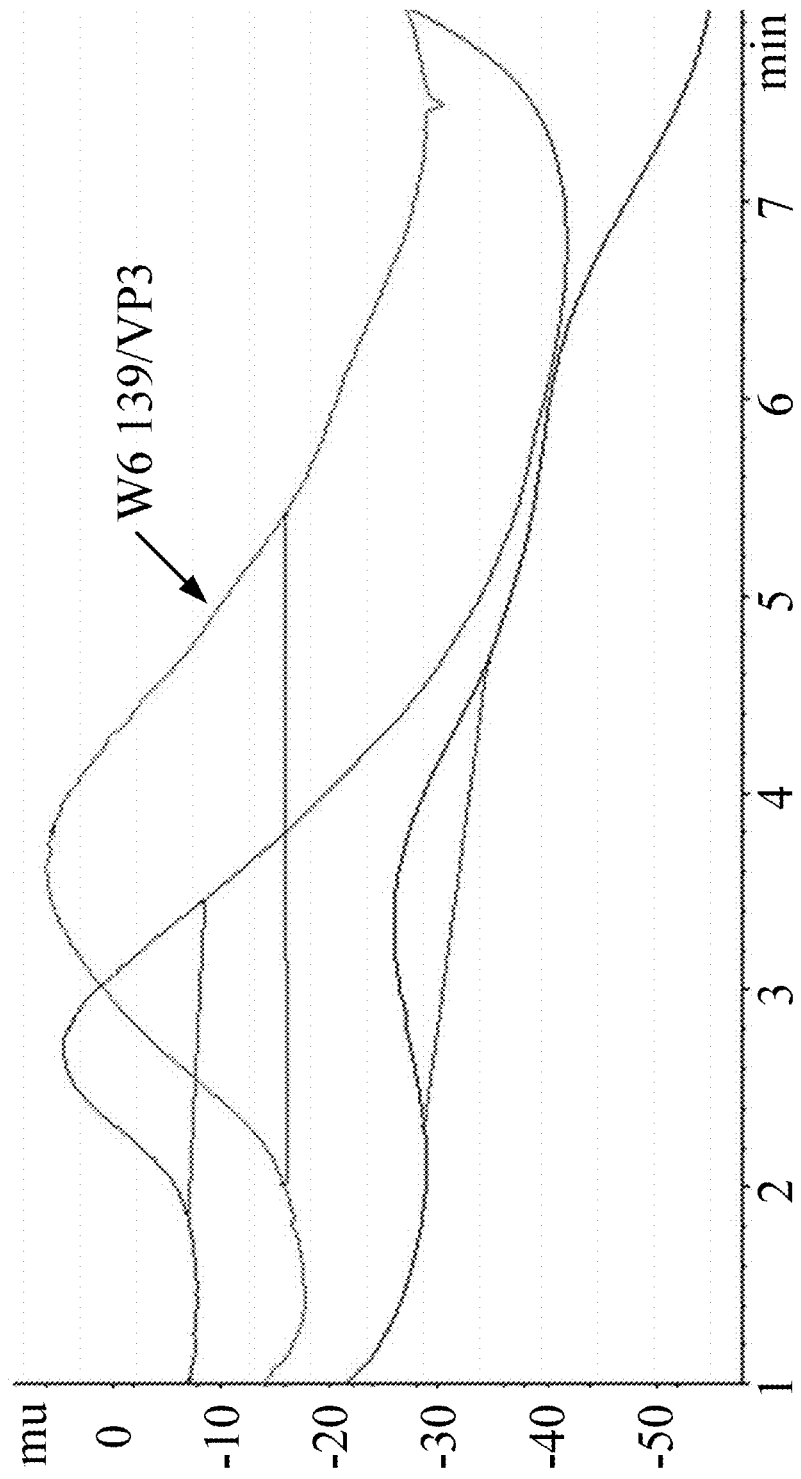
FIG. 2 shows the sucrose density gradient centrifugation of FMD VLPs containing a mineralization peptide.
Figure 3:
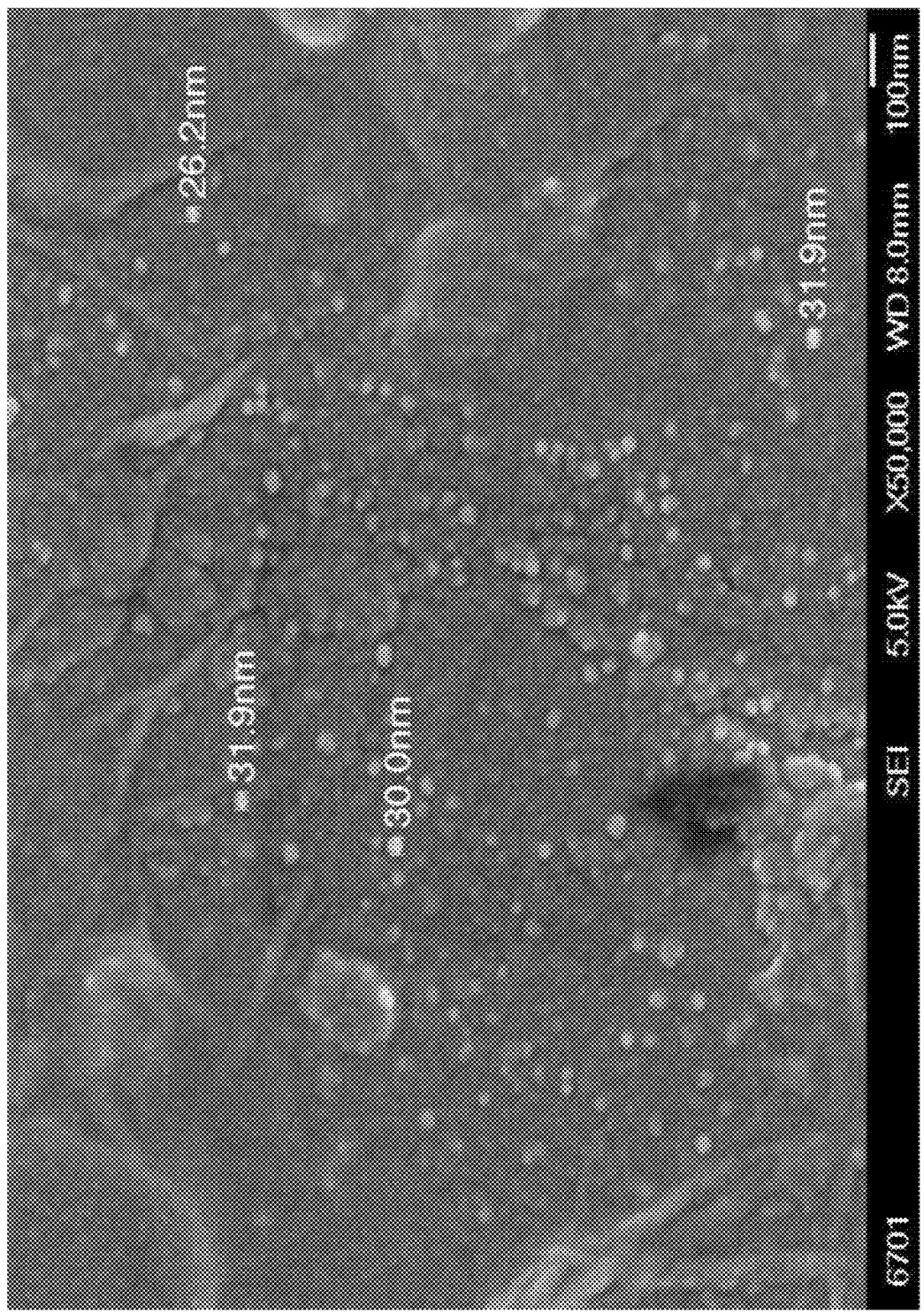
FIG. 3 is an SEM image of mineralized VLPs.
Figure 4:
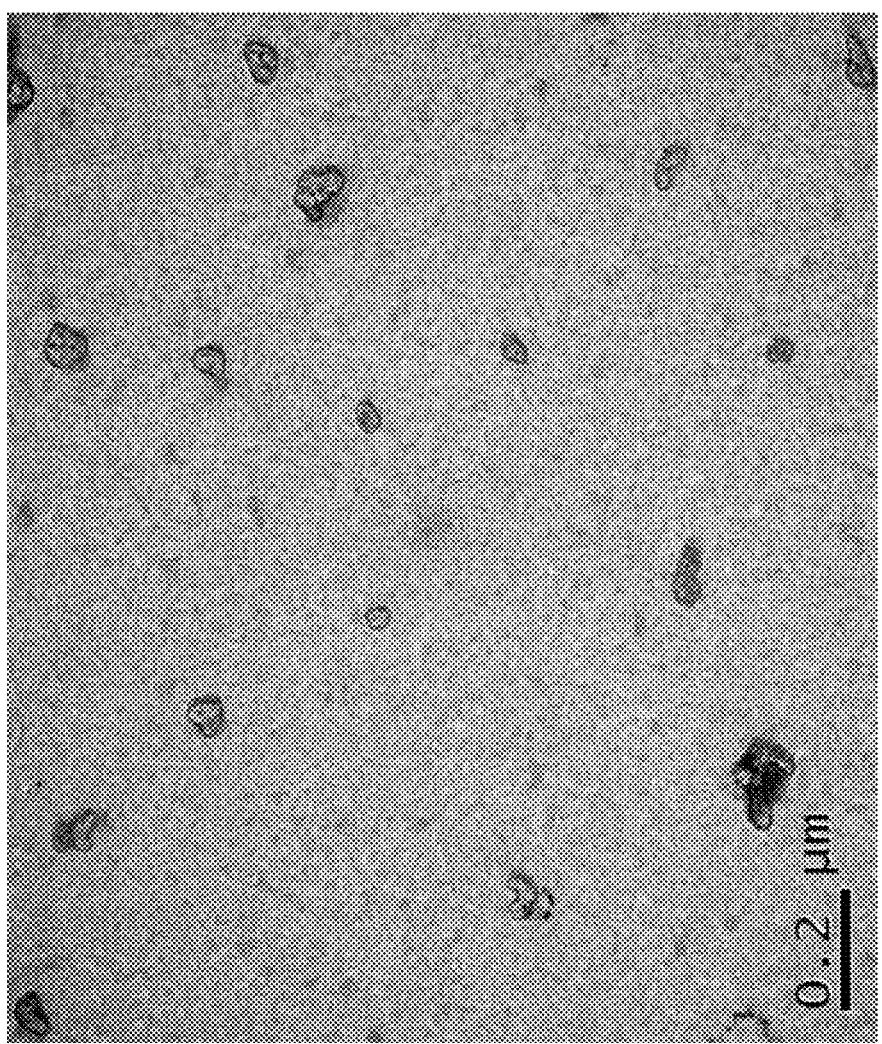
FIG. 4 is a TEM image of mineralized VLPs (non-stained)
Figure 5:
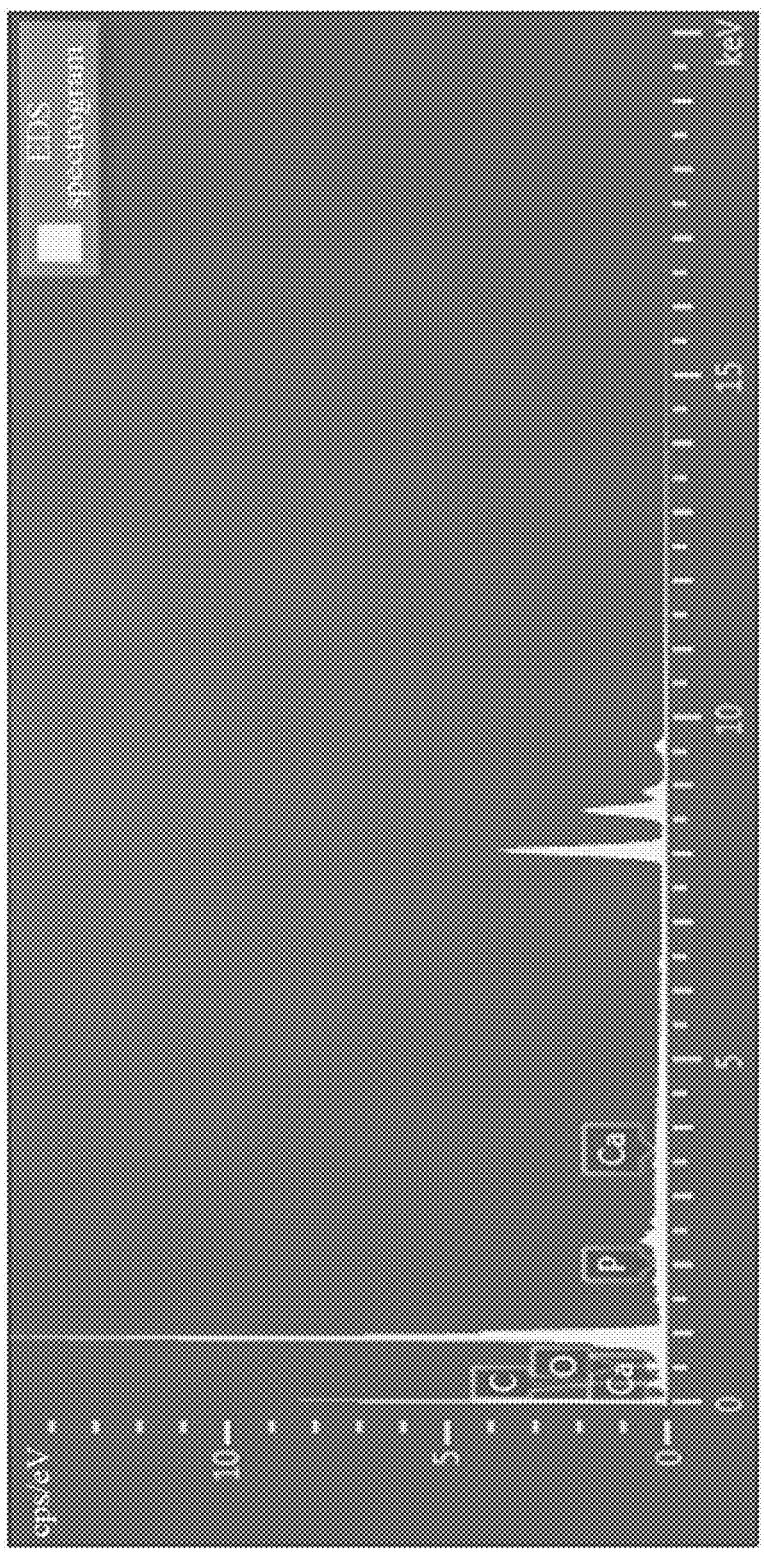
FIG. 5 shows energy dispersive spectrometer (EDS) analysis of the surface of mineralized VLPs.
Figure 6:
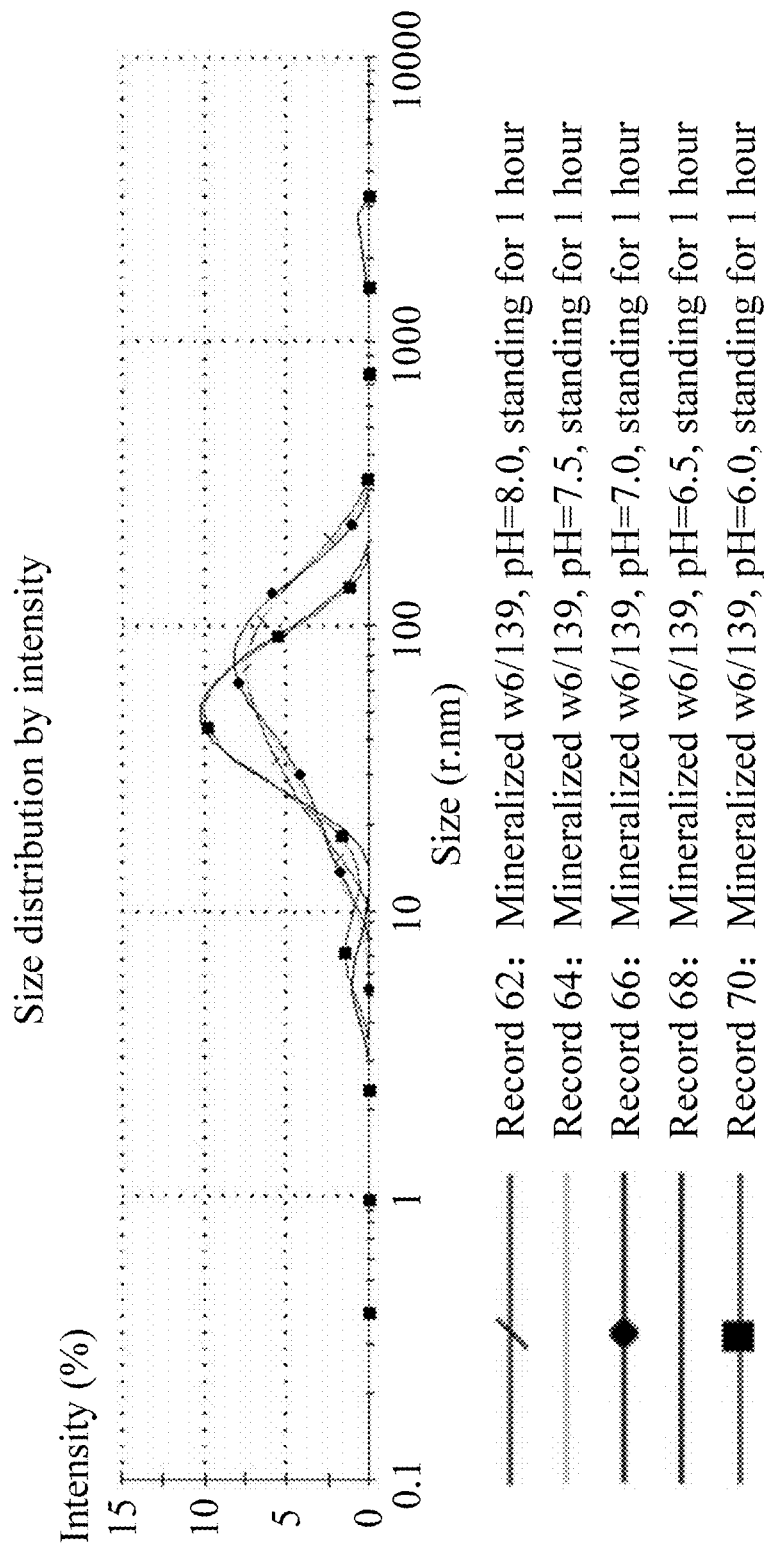
FIG. 6 shows dynamic light scattering(DLS) analysis of supernatants obtained from centrifugation of mineralized systems at various pH values.
Figure 7:
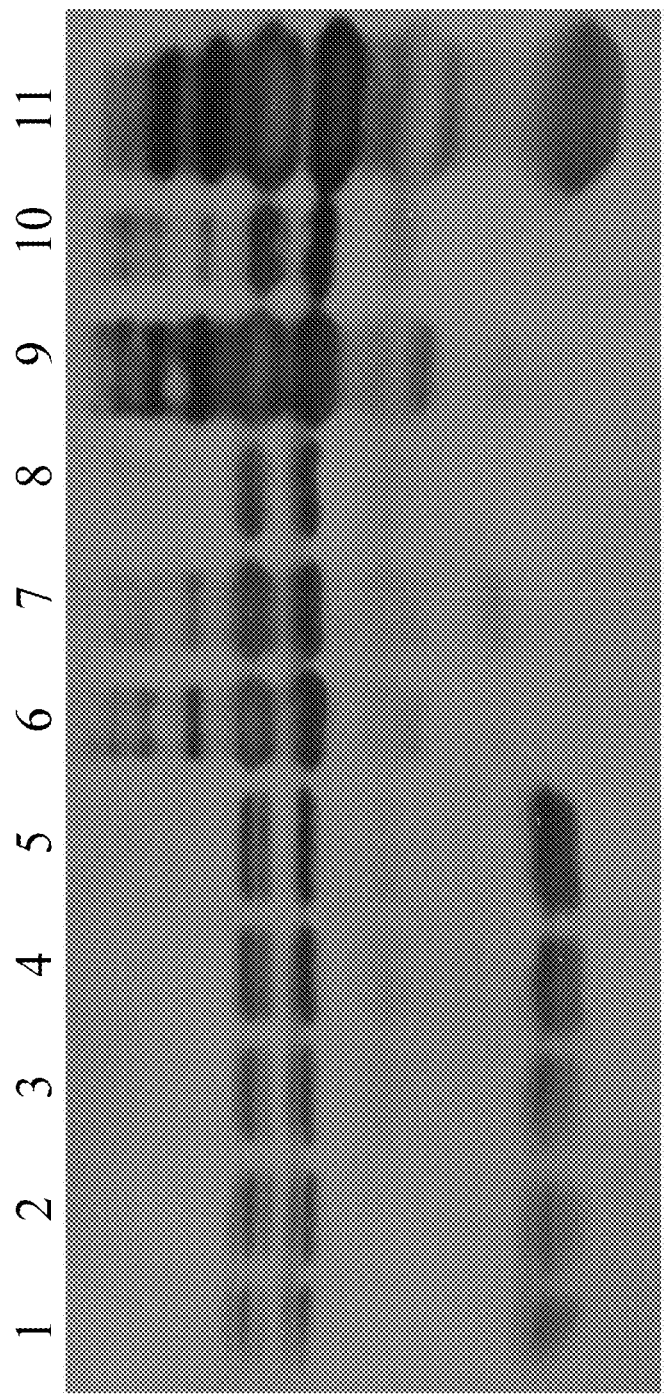
FIG. 7 shows Western-blotting analysis of mineralized systems at various pH values;
 1. Supernatant at pH 8.0; 2. Supernatant at pH 7.5; 3. Supernatant at pH 7.0; 4. supernatant at pH 6.5; 5. Supernatant at pH 6.0; 6. Pellet at pH 8.0; 7. Pellet at pH 7.5; 8. Pellet at pH 7.0; 9. Pellet at pH 6.5; 10. Pellet at pH 6.0; and 11. Non-mineralized VLPs.
Figure 8A:
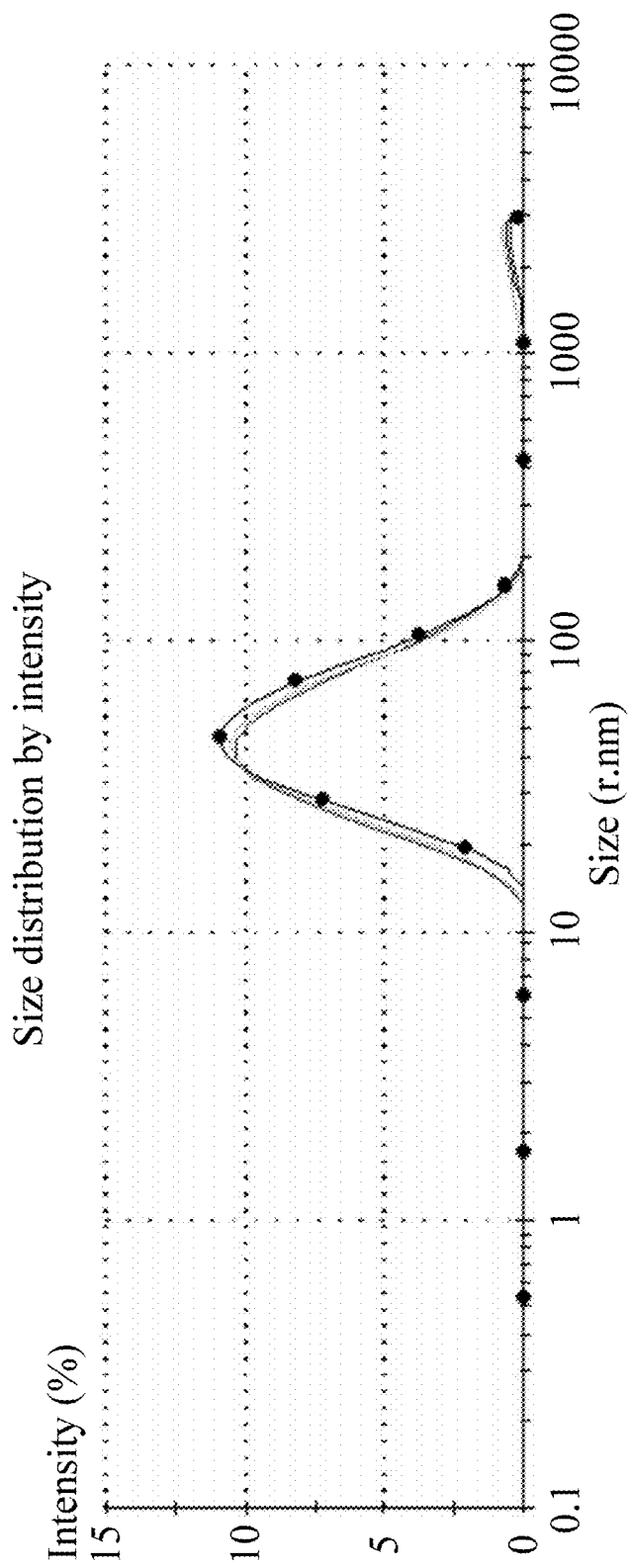
FIGS. 8A-8D show DLS analysis of the stability of mineralized VLPs at various temperatures;
 8A. DLS analysis of a supernatant after standing for 1 day; 8B. DLS analysis of a supernatant after standing for 3 days; 8C. DLS analysis of a supernatant after standing for 5 days; and 8D. DLS analysis of a supernatant after standing for 7 days.
Figure 8B:
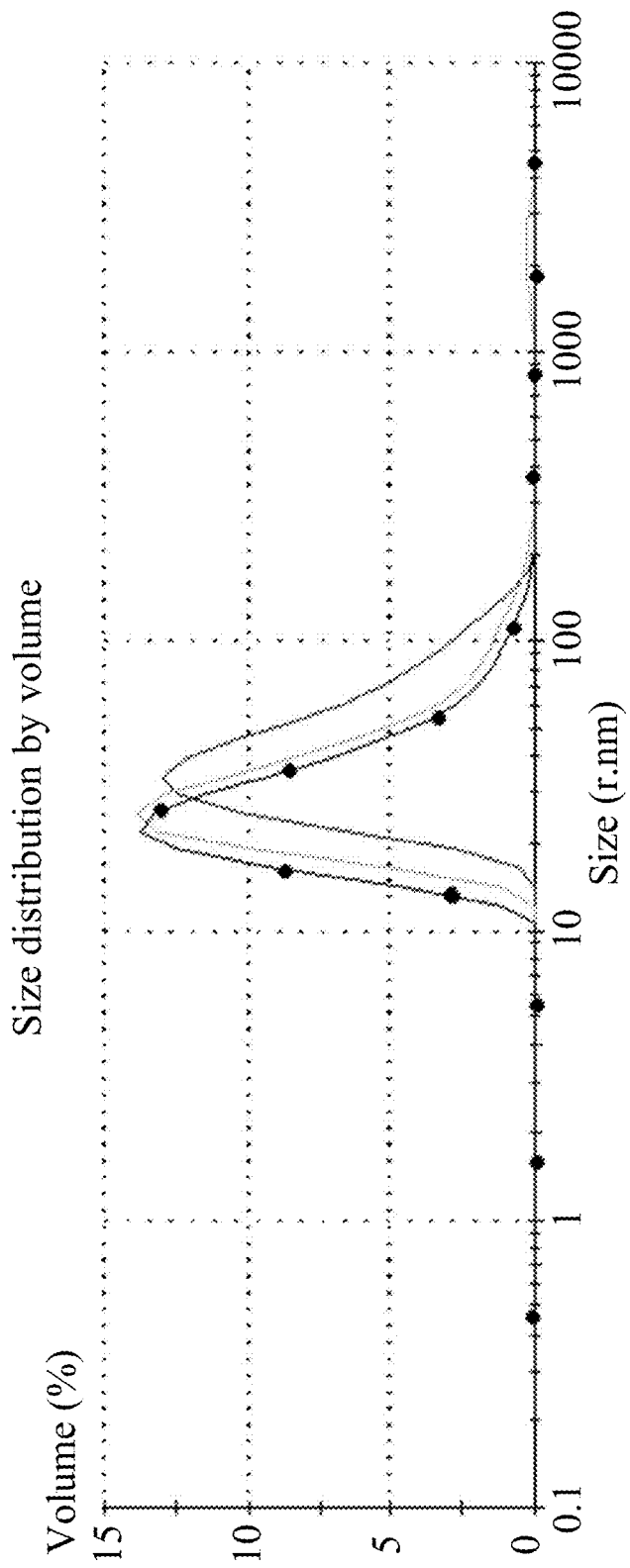
Figure 8C:
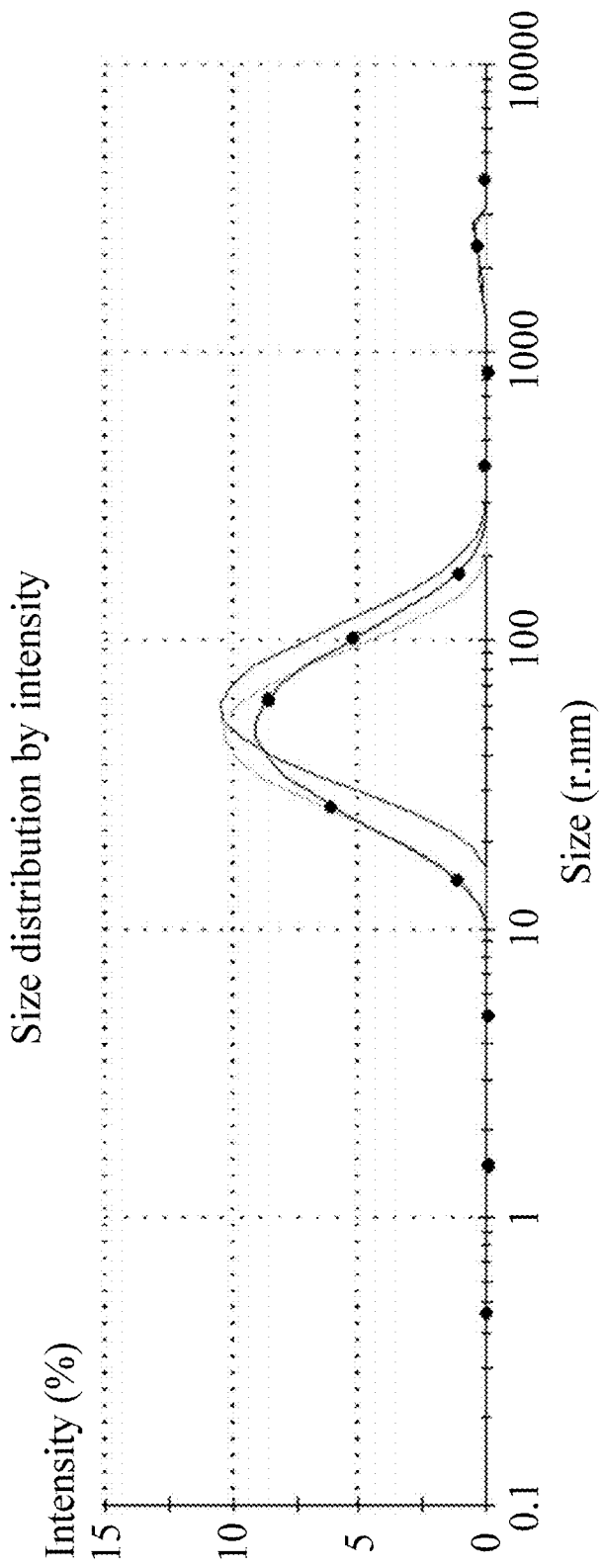
Figure 8D:
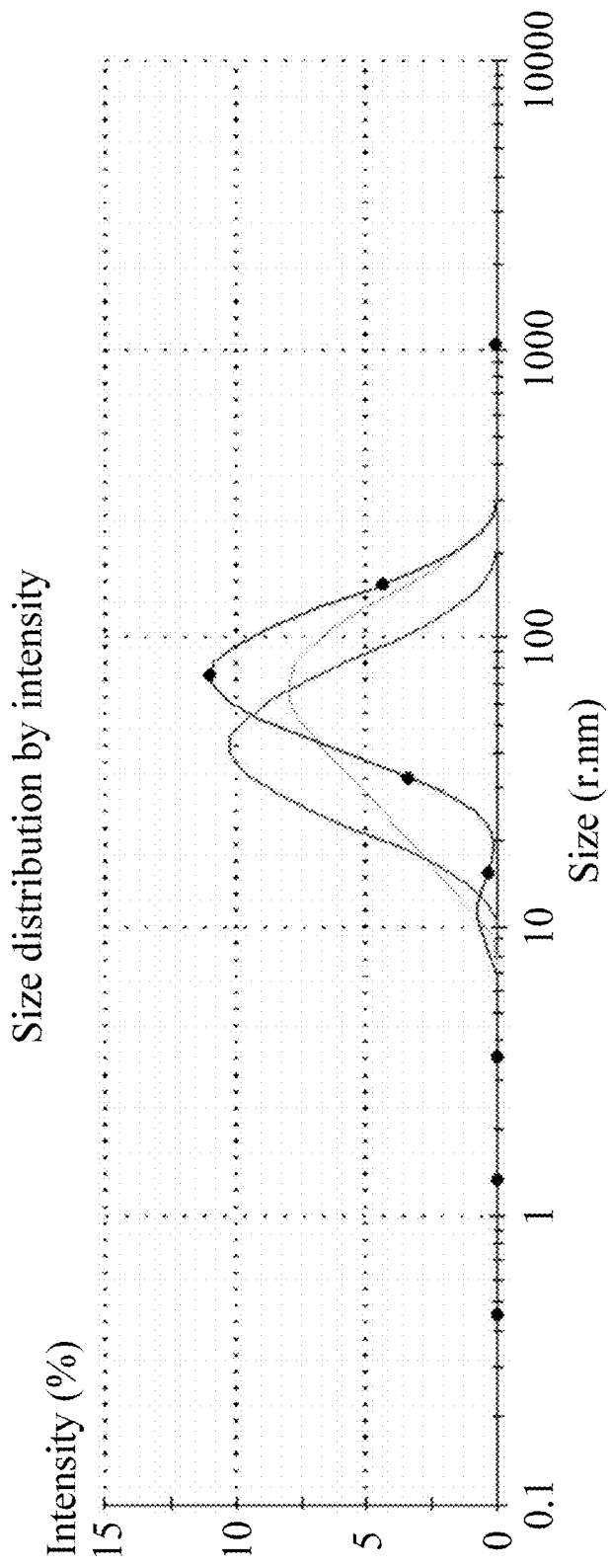

To further illustrate, experiments detailing foot-and-mouth disease (FMD) virus like particles (VLPs) and preparation method and use thereof are described below. It should be noted that the following examples are intended to describe and not to limit the description.

Example 1 Construction of Foot-and-Mouth Disease (FMD) Virus Like Particles (VLPs)

1. Construction of Recombinant Plasmids pSMK/VP0-VP1 and pSMA/VP3
 (1) Construction of Small Ubiquitin-Like Modifier protein Fusion Expression Vectors pSMA and pSMK
 a. The smt3 gene was amplified with the genomic DNA of *Saccharomyces cerevisiae* as a template and using smt3F and smt3R as primers. The primer sequences were:

smt3F:
(SEQ ID NO. 10)
5'GCCATGGGTCATCACCATCATCATCACGGGTCGGACTCAGAAGTCAATCAA3';

smt3R:
(SEQ ID NO. 11)
5'GGATCCGAGACCTTAAGGTCTCAACCTCCAATCTGTTCGCGGTG 3';

b. The smt3 gene was digested by restriction enzymes Nco I and BamH I and inserted into the pET-28a vector that was digested by restriction enzymes Nco I and BamH I to obtain the vector pSMK, and replacing the kanamycin resistance gene of the pSMK by the ampicillin resistance gene, to obtain the vector pSMA.

(2) Construction of Recombinant Expression Vectors Comprising Genes Encoding the Structural Proteins of FMD Virus The structural protein VP0, VP3, and VP1 coding genes were synthesized according to the sequence of serotype O FMD virus deposited under GenBank Accession No. JN998085.1, following the method as described in Hoover DM1, Lubkowski J. DNAWorks: an automated method for designing oligonucleotides for PCR-based gene synthesis. Nucl. Acids Res. (2002) 30 (10): e43.

The VP0, VP1 and VP3 coding genes were amplified with the synthesized genes as templates and using the following primers as below:

VP1F:
(SEQ ID NO. 12)
5'GGTCTCTAGGTACCACCAGCACGGGCGAA 3'

VP1R:
(SEQ ID NO. 13)
5'CGCGGATCCTCACAGACTTTGTTTGACCGG 3'

VP0F:
(SEQ ID NO. 14)
5'GGTCTCTAGGTGGTGCGGGCCAGTCATCTCC 3'

VP0R:
(SEQ ID NO. 15)
5'CGCGGATCCTCATTCTTTACTCGGAAATTC 3'

VP3F:
(SEQ ID NO. 16)
5'GGTCTCTAGGT GGTATCTTCCCGGTGGCGTG 3'

VP3R:
(SEQ ID NO. 17)
5'CGCGGATCCTCA TTGCTGACGGGCATCAACC 3'

The VP1, VP0, and VP3 coding genes were obtained by Polymerase Chain Reaction (PCR) amplification using the primers VP1F/VP1R, VP3F/VP3R, and VP0F/VP0R respectively, in which the gene encoding VP1 has a sequence as shown in SEQ ID NO.1, the gene encoding VP0 has a sequence as shown in SEQ ID NO.2, and the gene encoding VP3 has a sequence as shown in SEQ ID NO.3. The amplified VP1, VP0 and VP3 coding genes were digested by BsmBI/BamH I, and inserted into the pSMK or pSMA that was digested by BsaI, to yield recombinant expression vectors which are designated as pSMK/VP0, pSMK/VP1, and pSMA/VP3 respectively. A DNA fragment comprising T7 promoter and prokaryotic expression elements and the VP1 coding gene was obtained by amplification with pSMK/VP1 as a template and using T7BamHI/VP1XhoI as primers, and the DNA fragment was digested by BamH I/Xho I, and inserted into the pSMK/VP0 that was also digested by BamH I/Xho I, to obtain a recombinant co-expression vector that was designated as pSMK/VP0-VP1. The T7BamHI/VP1XhoI primer sequences were:

T7BamHI:
(SEQ ID NO. 18)
5'GCAATTGGATCCCGTCCGGCGTAGAGGATCGA 3'

VP1XhoI:
(SEQ ID NO. 19)
5'GCGCACCTCGAGTCACAGAGTCTGTTTCTCAGG 3'

2. Construction of VP1 Recombinant Plasmid Comprising the Gene Sequence of a Mineralization Peptide Mineralization peptides N6 (SEQ ID NO.4), NW (SEQ ID NO.5), and W6(SEQ ID NO.6) were respectively inserted to the gene point of the VP1 gene sequence corresponding to the $15^{th}$ amino acid of the structural protein VP1 using inverse PCR (polymerase chain reaction), using the recombinant co-expression vector pSMK/VP0-VP1 as a template, to yield a VP1 recombinant plasmid comprising the gene sequence of the mineralization peptide, which is represented by SEQ ID NO. 7, SEQ ID NO. 8, or SEQ ID NO. 9. The primers used in the amplification of the mineralization peptide N6 were A1/A2; the primers used in the amplification of the mineralization peptide W6 were B1/B2; and the primers used in the amplification of the mineralization peptide NW were C1/C2.

A1:
(SEQ ID NO. 20)
5'GGCATGAAGCCAAGTCCACGCCCATTGGCCCAGAAAGCGGCAA G 3'

A2:
(SEQ ID NO. 21)
5'GACACTGGTCCCACGTTTTACGCTTACTTGCAGGTCACCTCTCGC 3'

B1:
(SEQ ID NO. 22)
5'CGCCGCATTGGCCGCTTTGGCTTGGCCCAGAAAGCGGCAAG 3'

B2:
(SEQ ID NO. 23)
5'AAGAAATTTTTCTTCGCTGCTGTCTACTTGCAGGTCACCTCTCGC 3'

C1:
(SEQ ID NO. 24)
5'GAACCGGAAAGCCAGCGTCGTATTGGCCGTTTTGGCTTGGCCCAGAAA GCGGCAAGA 3'

C2:
(SEQ ID NO. 25)
5'TTCTTTATCATCGGTGCCTTCCAGACGCCAACGTACTTGCAGGTCACC TCTCGCAT 3'

The VP1 recombinant plasmid comprising the gene sequence of the mineralization peptide were obtained, which were designated as pSMK/VP0-N6VP1, pSMK/VP0-NWVP1, and pSMK/VP0-W6VP1, respectively.

3. Expression and Purification of Capsid Protein (1) The expression vectors pSMK/VP0-N6VP1, pSMK/VP0-NWVP1, and pSMK/VP0-W6VP1 were respectively co-transformed with the vector pSMA/VP3 into an expression strain BL21(DE3). The strain was inoculated onto a culture plate containing kanamycin, chloromycetin, and ampicillinum, and incubated overnight. A positive clone was screened out, and single clones were picked into an LB medium containing kanamycin, chloromycetin, and ampicillinum, and incubated at 37° C. and 220 rpm. A positive clone was identified, screened and sequenced by PCR.

(2) The positive clone containing N6, NW, and W6 peptides was scaled up at 37° C. and 220 rpm, until the OD600 of the bacterial solution was about 0.8. Then, the bacterial solution was induced with IPTG at a final concentration of 0.25 mM, incubated at 4° C. and 200 rpm for 16 hrs, and then centrifuged at 8000 rpm for 15 min to collect a bacterial pellet. The bacterial pellet was re-suspended in 10-20 mL of a buffer solution A (20 mM Tris-HCl, 500 mM NaCl, 5 mM imidazole, pH=8.4) in an ice bath, and ultrasonically homogenized (3 s-ultrasonication, followed by 3s-break-off, 20 min in total, power 300 W). After centrifugation at 12,000 xg for 30 min, a supernatant was collected. The target protein was manually purified by Ni-NTA His·Bind R filler.

(3) The supernatant was allowed to bind to the filler at 4° C. for about 1 hr, by flowing through under gravity. The non-specifically bound impurity proteins were removed by washing with buffer solution A that was 10 times the volume of the column, and then the target proteins were eluted off using a buffer solution B (20 mM Tris-HCl, 500 mM NaCl, 300 mM Imidazol, pH=8.4) and stored at −70° C. As determined by SDS-PAGE and Western blotting, proteins with expected sizes were obtained (-s shown in FIG. 1).

A fusion protein containing no mineralization peptide was also prepared.

4. In-Vitro Assembly of FMD VLPs and Determination of Assembly Efficiency

Following the instruction for use recommended by Invitrogn, the fusion protein was digested by a small ubiquitin-like modifier protease as follows. 20 μg of the purified fusion protein with or without mineralization peptide was digested at 37° C. for 30 min by using 200 μL of a buffer (50 mM Tris-HCl, 150 mM NaCl, pH 8.0, 0.2% Igepal (NP-40), 1 mM DTT), and 10 μL of small ubiquitin-like modifier protease (1 U/μL). The small ubiquitin-like modifier protein tag was removed from the digested mixture by HisTrap HP chromatography, and a flow-through liquid containing VP0, VP1, and VP3 was collected into an assembly buffer solution (20 mM Tris-HC1, 500 mM NaCl, pH8.0). VLPs were assembled at 4° C. overnight.

The VLPs were separated by sucrose density gradient centrifugation. Specifically, 1.5 mL of an assembled sample with or without a mineralization peptide was placed over a sucrose concentration gradient of 45%-15%, and centrifuged at 38000 rpm and 4° C. for 3.5 hrs. Then the sample was detected by a UV detector by means of continuous injection, and a spectrum was plotted to determine the assembly of the VLPs based on the peak area. The results show that the W6 peptide-containing VLPs (W6 139/VP3) have the highest assembly efficiency, as shown in FIG. 2.

A sample peak containing VLPs was collected, quantified by double-antibody sandwich ELISA, and finally the assembly efficiency was determined.

Assembly efficiency of VLPs=amount of antigen comprising VLP sample peak/total amount of antigen loaded×100%

The results show that the assembly rate of VLPs containing W6 peptide is 45% and the assembly rate of non-mutated VLPs is 30%.

5. Mineralization and Characteristics AnMFMD CVLVIalysis of FMD VLPs (1) Mineralization of FMD VLPs VLPs with or without a mineralization peptide were added in an equal amount based on antigen to a first solution (pH 7.4) (containing 80-100 mM $Na^+$, 1-10 mM $K^+$, 1-5 mM $Ca^{2+}$, 1-10 mM $Mg^{2+}$, 100-200 mM $Cl^-$, 10-20 mM $HCO^{3-}$, 1-10 mM $HPO4^{2-}$, and 1-10 mM $PO4^{3-}$), and incubated for 10 min at room temperature. Then, an equal volume of a second solution (pH 7.4) (containing 80-150 mM $Na^+$, 2-20 mM $Mg^{2-}$, 1-20 mM $Ca^{2'}$, 100-200 mM $Cl^-$, 100-200 mM $HCO^{3-}$, 1-10 mM $HPO4^{2-}$, and 1-10 mM $PO4^{3-}$) was added to the first solution, incubated at 4° C. overnight, and centrifuged for 10 min at 16000 rpm. The supernatant and pellet were collected respectively. The antigen content was determined by double-antibody sandwich ELISA, the mineralization efficiency was calculated, and then the morphology was analyzed by TEM. X-ray energy analysis was performed to determine the elemental composition on the surface of the mineralized VLS. The results show that the mineralization effect of W6 mineralization peptide (W6 139/VP3) is the best, and the maximum antigen level mineralized is up to 94 μg/mL. However, the mineralization effect of the mineralization peptide NW (NW150/VP3) leaves much to be desired. Although the VLPs without a mineralization peptide (VP01/VP3) can also be mineralized, the mineralization rate is relatively random and the maximum antigen level mineralized is less than 50 μg (Table 1). SEM (FIG. 3) and TEM (FIG. 4) show that there are a large number of virus particles in the pellet collected after mineralization, and EDS analysis reveals that the virus particles have Ca, P, O, and other elements distributed on the surface (FIG. 5).

The results show that after the mineralization peptide is inserted, the expression of the target protein and the assembly of VLPs are not affected. The mineralization effects exhibited by the three mineralization peptides are quite different. The mineralization level of VLPs containing one of the mineralization peptides is as high as 100 μg, with a mineralization level of 99.7%. Although the mineralization rate of VLPs without mineralization peptides can reach 75%, the mineralization is unstable, and the mineralization level of VLPs is only 45 μg at most. The disclosure provides a new technical means for the development of ambient-temperature FMD VLP vaccines at normal temperature.

TABLE 1

Comparison of Mineralization Effects of Different Types of VLPs

| Name | NW150/ VP3 | N6P150/ VP3 | W6 139/ VP3 | VP01/ VP3 |
|---|---|---|---|---|
| Maximum antigen level (μg/mL) | 46 | 84 | 94 | 45.12 |
| Average mineralization rate (%) | 79 | 88 | 99 | 83.6 |

(2) Acid Resistance Analysis of Mineralized VLPs

The pH of the mineralized VLPs (W6 139/VP3) was adjusted to 8.0, 7.5, 7.0, 6.5 and 6.0, respectively, and allowed to stand at room temperature for 1 hr, and then detected by dynamic light scattering (DLS), ELISA and western blotting, to determine the pH resistance of the mineralized layer. The results show that when the pH value reaches 6.5, dissolution of the mineralized shell occurs, and the content of the small molecule material in the mineralized system is increased significantly. The DLS analysis peak is shifted to the left at 6.5 and 6.0 (FIG. 6). ELISA and western blotting (FIG. 7) also show the highest detection value at 6.5.

(3) Thermal Stability Analysis of Mineralized VLPs

Figure 9A:
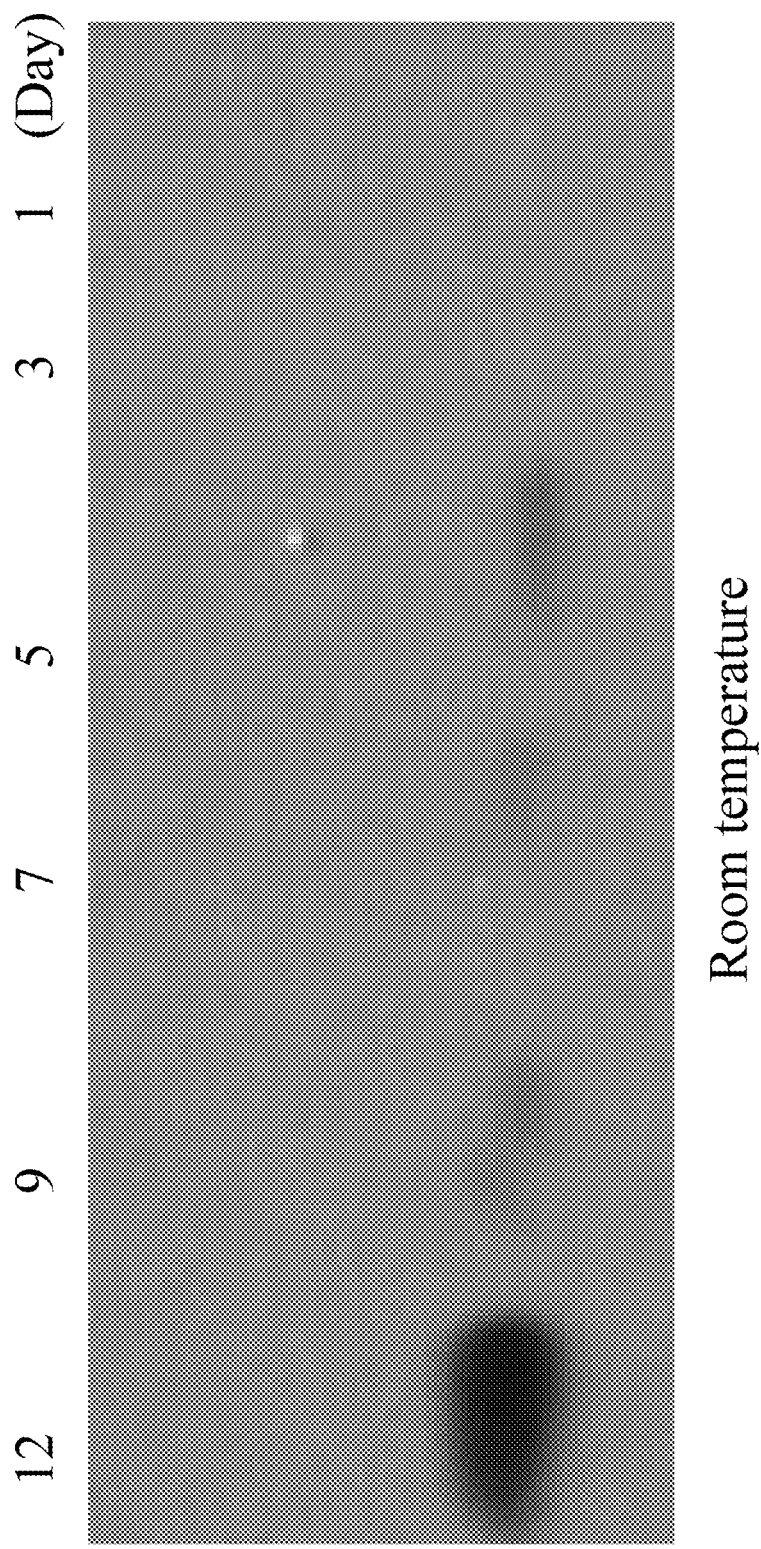
FIGS. 9A-9B show Western-blotting analysis of the stability of mineralized VLP at different temperature.
Figure 9B:
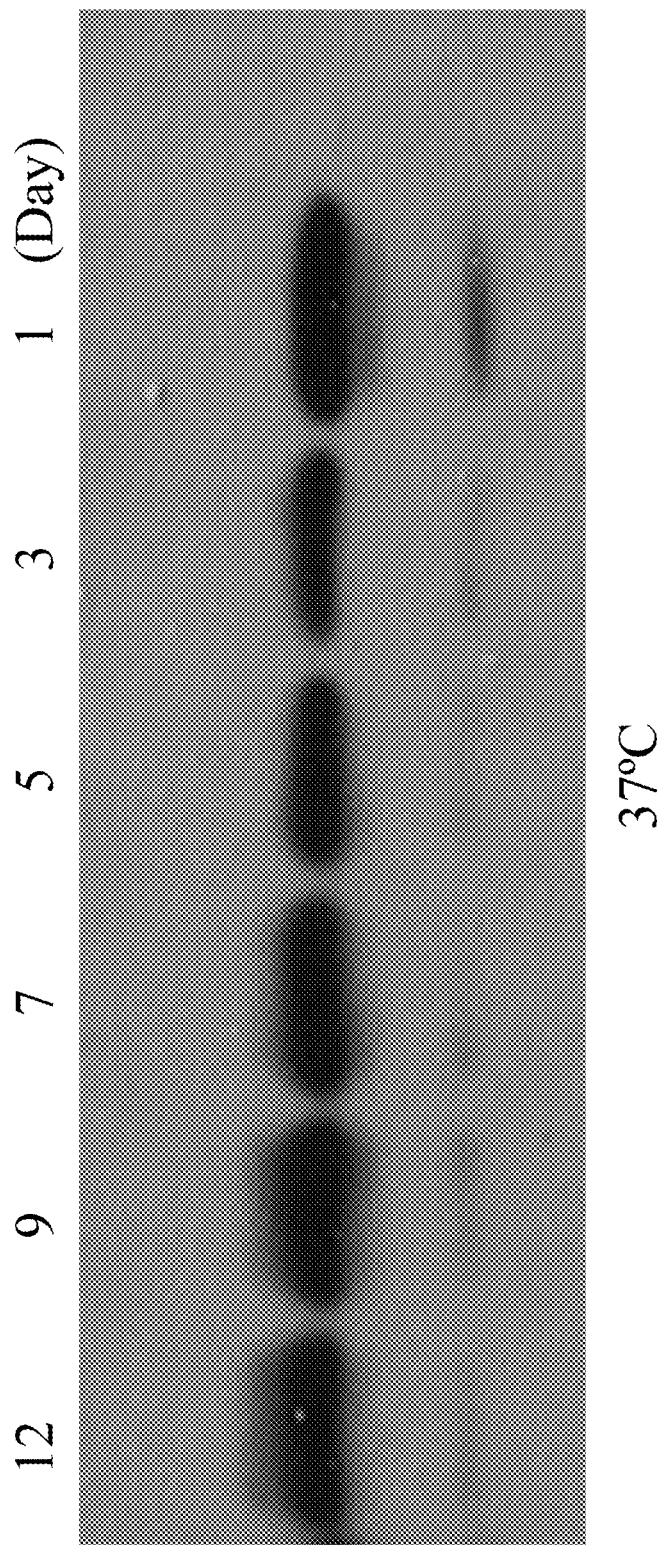

The mineralized VLPs (W6 139/VP3) were stood at 4° C., 26° C. and 37° C., respectively, and sampled at Days 1, 3, 5, 7 and 9. The supernatant was detected by dynamic light scattering (DLS) and western blotting, to determine the effect of mineralization on the thermal stability of VLPs. The results show that the mineralized VLPs can be stood at 26° C. for 9 days and at 37° C. for approximately 7 days. After standing at 37° C. for 7 days, the content of the small molecule material in the mineralized system is increased significantly, and the DLS analysis peak is clearly shifted to the left (FIGS. 8A-8D). Western blotting (FIGS. 9A-9B) show that the antigen content in the supernatant is significantly increased, after standing at normal temperature for 12 days. After standing at 37° C. for 7 days, the antigen content in the supernatant is increased significantly.

In the disclosure, three mineralization peptides capable of accumulating calcium ions are respectively inserted into the structural protein VP1 of the serotype 0 FMD virus through genetic engineering technology. Intact VLPs are successfully expressed and assembled in E. coli, without affecting the assembly efficiency. Then, the VLPs are mineralized with a mineralizing agent, and the assembly effect of the FMD VLPs is improved. The FMD VLPs and use thereof promote the transition of protein vaccines from cold-chain vaccines to normal temperature vaccines.

Example 2 Immunogenic Analysis of Mineralized FMD VLPs

Figure 10:
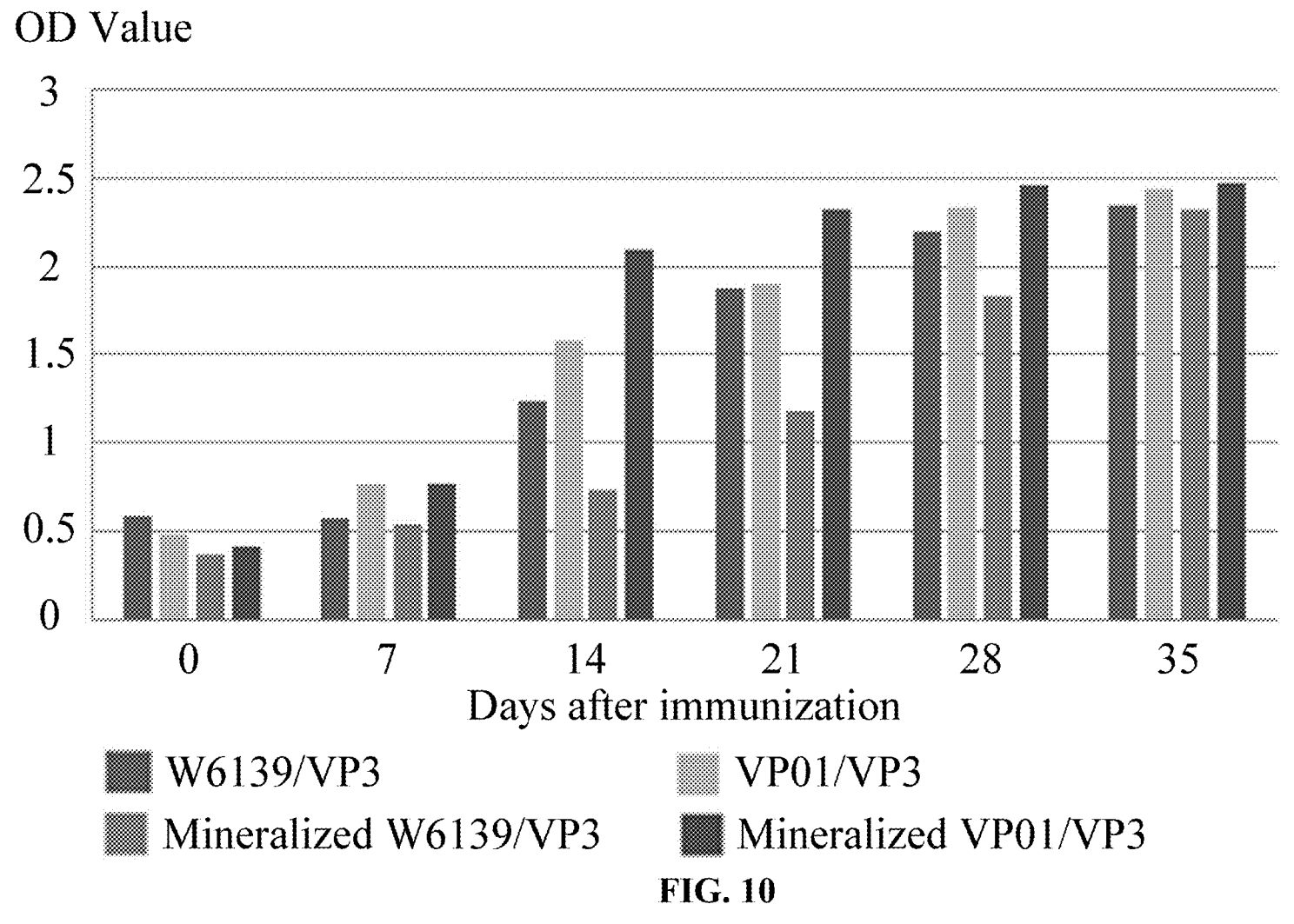

The mineralization peptide-containing W6 139/VP3 and mineralization peptide-free VP01/VP3 FMD VLPs were mineralized following the method in Example 1 and emulsified with ISA-206 adjuvant. The guinea pigs weighed 200 g were immunized to determine the effect of mineralization on the immunogenicity of VLPs. The non-mineralized W6 139/VP3 and VP01/VP3 VLPs were used as controls. Each vaccine had an immunization dose of 0.5 mL, a total protein content of 50 μg, and a VLP content of about 3 μg. Blood was collected at 0, 7, 14, 21, 28, and 35 days after immunization, and the content of specific antibodies was determined by LPB-ELISA. The results show that the mineralized shell has an action of sustained release, and the level of antibody production against the mineralized VLPs is low at an early stage of immunization, but comparable to that against non-mineralized VLPs at a later stage (FIG. 10).

Unless otherwise indicated, the numerical ranges involved include the beginning and end values. It will be obvious to those skilled in the art that changes and modifications may be made, and therefore, the aim in the appended claims is to cover all such changes and modifications.

---

What is claimed is:

1. Foot-and-mouth disease (FMD) virus like particles (VLPs), the VLPs comprising:
    a structural protein VP0;
    a structural protein VP1 comprising a mineralization peptide;
    a structural protein VP3; and
    a calcium phosphate coat;
  wherein:
    the structural protein VP1 comprising a mineralization peptide is encoded by a gene sequence represented by SEQ ID NO: 7, SEQ ID NO: 8 or SEQ ID NO: 9;
    the structural protein VP0 is encoded by a gene sequence represented by SEQ ID NO: 2;
    the structural protein VP3 is encoded by a gene sequence represented by SEQ ID NO: 3; and
    the calcium phosphate coat covers the structural protein VP0, the structural protein VP1 comprising a mineralization peptide, and the structural protein VP3.

2. The VLPs of claim 1, wherein the structural protein VP1 comprising a mineralization peptide is encoded by the gene sequence represented by SEQ ID NO: 9.

3. The VLPs of claim 1, wherein the mineralization peptide of the structural protein VP1 is encoded by a gene sequence represented by SEQ ID NO: 4, SEQ ID NO: 5, or SEQ ID NO: 6.

4. A method for preparing foot-and-mouth disease (FMD) virus like particles (VLPs), the method comprising:
    (1) constructing a recombinant plasmid comprising genes encoding a structural protein VP0, a structural protein VP1 comprising a mineralization peptide, and a structural protein VP3 of foot-and-mouth disease virus (FMDV), wherein: the structural protein VP1 comprising a mineralization peptide is encoded by a gene sequence represented by SEQ ID NO: 7, SEQ ID NO: 8 or SEQ ID NO: 9; the structural protein VP0 is encoded by a gene sequence represented by SEQ ID NO: 2; the structural protein VP3 is encoded by a gene sequence represented by SEQ ID NO: 3;
    (2) expressing and purifying the structural protein VP0, the structural protein VP1 comprising a mineralization peptide, and the structural protein VP3 of FMDV;
    (3) assembling FMD VLPs; and
    (4) mineralizing the FMD VLPs.

5. The method of claim 4, comprising:
    a) employing genomic DNA of *Saccharomyces cerevisiae* as a template and using smt3F and smt3R as primers, amplifying a smt3 gene, wherein gene sequences of the primers smt3F and smt3R are represented by SEQ ID NO: 10 and SEQ ID NO: 11, respectively;
    b) digesting the smt3 gene and a vector pET-28a using Nco I and BamH I, inserting the digested smt3 gene into the digested pET-28a vector, to yield a vector pSMK; and replacing a kanamycin resistance gene of the vector pSMK by an ampicillin resistance gene, to yield a vector pSMA;
    c) synthesizing coding genes of structural proteins VP0, VP3, and VP1 according to a gene sequence of serotype O FMD virus, where the coding gene of the structural protein VP1 is represented by SEQ ID NO: 1, the coding gene of the structural protein VP0 is represented by SEQ ID NO: 2, and the coding gene of the structural protein VP3 is represented by SEQ ID NO: 3; employing the synthesized coding genes of structural proteins VP0, VP3, and VP1 as templates, employing VP1F/VP1R, VP0F/VP0R, and VP3F/VP3R as primers, and amplifying the coding genes of the structural proteins VP0, VP3, and VP1, respectively; wherein a gene sequence of the primer VP1F is represented by SEQ ID NO: 12, a gene sequence of the primer VP1R is represented by SEQ ID NO: 13, a gene sequence of the primer VP0F is represented by SEQ ID NO: 14, a gene sequence of the primer VP0R is represented by SEQ ID NO: 15, a gene sequence of the primer VP3F is represented by SEQ ID NO: 16, a gene sequence of the primer VP3R is represented by SEQ ID NO: 17;
    d) digesting the amplified coding genes of the structural proteins VP0, VP3, and VP1 using the restriction enzymes BsmBI/BamH I, digesting the vector pSMK and pSMA using the restriction enzyme BsaI, inserting the digested coding genes of the structural proteins VP0, VP3, and VP1 into the digested vector pSMK or pSMA, to yield recombinant expression vectors pSMK/VP0, pSMK/VP1, and pSMA/VP3, respectively;
    e) employing the recombinant expression vector pSMK/VP1 as a template, employing T7BamHI/VP1XhoI as primers, and amplifying a DNA fragment comprising T7 promoter and the coding gene of the structural protein VP1; digesting the DNA fragment and the recombinant expression vector pSMK/VP0 using restriction enzymes BamHI/XhoI, to yield a recombinant co-expression vector pSMK/VP0-VP1, where a gene sequence of the primer T7BamHI is represented by SEQ ID NO: 18, and a gene sequence of the primer VP1XhoI is represented by SEQ ID NO: 19;
    f) providing a mineralization peptide represented by SEQ ID NO: 4, SEQ ID NO: 5, or SEQ ID NO: 6, employing the recombinant co-expression vector pSMK/VP0-VP1 as a template, inserting the gene sequence of the mineralization peptide into a gene point of the VP1 gene sequence corresponding to the $150^{th}$ amino acid of the structural protein VP1 using inverse polymerase chain reaction (PCR), to yield a VP1 recombinant plasmid comprising the gene sequence of the mineralization peptide, wherein the VP1 recombinant plasmid comprising the gene sequence of the mineralization peptide is represented by SEQ ID NO: 7, SEQ ID NO: 8, or SEQ ID NO: 9;
    g) co-transforming the recombinant plasmid comprising the gene sequence of the mineralization peptide and the vector pSMA/VP3 into an expression strain BL21 (DE3), inoculating the expression strain onto a culture plate containing kanamycin, chloromycetin, and ampicillinum, incubating overnight, screening out and scale-up culturing positive clones containing the mineralization peptide, purifying the positive clones, to yield target proteins;
    h) digesting the target proteins using a ubiquitin protease, removing ubiquitin-modified proteins using HisTrap HP chromatography, collecting and putting a flow-through liquid containing the structural proteins VP0, VP1, and VP3 from the chromatography into a pH 8.0 buffer solution containing 20 mM Tris-HCl and 500 mM NaCl, and allowing the buffer solution to stand at 4° C. overnight, to yield VLPs; and
    i) adding the VLPs to a first solution, pH 7.4, comprising 80-100 mM $Na^+$, 1-10 mM $K^+$, 1-5 mM $Ca^{2+}$, 1-10 mM $Mg^{2+}$, 100-200 mM $Cl^-$, 10-20 mM $HCO^{3-}$, 1-10 mM $HPO_4^{2-}$, and 1-10 mM $PO_4^{3-}$, and incubating for 10 min at room temperature; adding a second solution, pH 7.4 and equal to the first solution in volume, comprising 80-150 mM $Na^+$, 2-20 mM $Mg^{2+}$, 1-20 mM $Ca^{2+}$, 100-200 mM $Cl^-$, 100-200 mM $HCO^{3-}$, 1-10 mM $HPO_4^{2-}$, and 1-10 mM $PO_4^{3-}$ to the first solution, incubating at 4° C. overnight, and centrifuging for 10 min at 16000 rpm, to yield mineralized VLPs.

6. The method of claim 5, wherein the structural protein VP1 comprising a mineralization peptide is encoded by SEQ ID NO: 9.

* * * * *

SEQUENCE LISTING

```
<160> NUMBER OF SEQ ID NOS: 25

<210> SEQ ID NO 1
<211> LENGTH: 639
<212> TYPE: DNA
<213> ORGANISM: Artificial Sequence
<220> FEATURE:
<223> OTHER INFORMATION: Fully synthetic

<400> SEQUENCE: 1
accaccagca cgggcgaatc ggcagatccg gttacggcaa cggtcgaaaa ctacggcggc      60
gaaacgcagg ttcaacgtcg tcatcatacc gatgttagct ttattctgga ccgtttcgtg     120
aaagttacgc cgaaggattc tatcaacgtc ctggacctga tgcagacccc gccgcatacc     180
ctggtgggcg cactgctgcg caccgccacg tattactttg cagatctgga agtcgctgtg     240
aaacacgaag gcgacctgac ctgggtcccg aatggtgcac cggaagcagc actggataac     300
accacgaatc cgacggcata tcataaagct ccgctgaccc gtctggcact gccgtacacg     360
gccccgcacc gtgttctggc aaccgtctat aacggcaatt gcaaatacgc tggcggtagt     420
ctgccgaacg tgcgtggtga tctgcaggtt ctggcccaaa aggcagcttg gccgctgccg     480
accagcttca attatggtgc gattaaagcc acccgtgtga cggaactgct gtatcgtatg     540
aagcgtgcag aaacctactg tccgcgtccg ctgctggcag tccacccgtc cgcagcacgc     600
cataagcaaa aaatcgtcgc cccggtcaaa caaagtctg                            639

<210> SEQ ID NO 2
<211> LENGTH: 909
<212> TYPE: DNA
<213> ORGANISM: Artificial Sequence
<220> FEATURE:
<223> OTHER INFORMATION: Fully synthetic

<400> SEQUENCE: 2
ggtgcgggcc agtcatctcc ggcgacgggt tcccagaatc aatcaggcaa cacgggttcc      60
```

| | |
|---|---|
| atcatcaaca actactacat gcaacagtat cagaacagtg tggatacccca actgggcgac | 120 |
| aacgcggttt caggcggttc gaatgaaggt agtaccgaca ccacgtccac gcataccacg | 180 |
| aatacccaga acaatgattg gtttagcaaa ctggcaagct ctgcttttc tggcctgttc | 240 |
| ggtgcgctgc tggccgacaa aaagaccgaa gaaaccacgc tgctggaaga tcgtattctg | 300 |
| accacgcgca acggccatac cacgagtacc acgcagagtt ccgtcggcat cacgcacggt | 360 |
| tacgcgaccg ccgaagattt cgtgtcaggc ccgaatacgc cgggtctgga aacccgtgtg | 420 |
| gttcaagccg aacgcttttt caaaacgcac ctgtttgatt gggtgacctc cgacccgttc | 480 |
| ggtcgttgct atctgctgga actgccgacg gatcacaagg gcgtttacgg tagcctgacc | 540 |
| gactcttatg cgtacatgcg caacggctgg gatgtggaag ttaccgccgt gggtaaccag | 600 |
| tttaatggcg gttgcctgct ggttgcaatg gtcctggaac tgtgttctat gaacgtcgc | 660 |
| gaactgttcc agctgacccct gtttccgcat caattcatta acccgcgtac caatatgacg | 720 |
| gctcacatca agttccgtt tgtcggcgtg aaccgctatg atcagtacaa agtccacaag | 780 |
| ccgtggaccc tggtcgtgat ggttgtcgca ccgctgaccg ttaatacgga aagcgctccg | 840 |
| caaatcaagg tgtatgccaa tatcgccccg acgaatgtcc acgttgctgg tgaatttccg | 900 |
| agtaaagaa | 909 |

<210> SEQ ID NO 3
<211> LENGTH: 660
<212> TYPE: DNA
<213> ORGANISM: Artificial Sequence
<220> FEATURE:
<223> OTHER INFORMATION: Fully synthetic

<400> SEQUENCE: 3

| | |
|---|---|
| ggtatcttcc cggtggcgtg tagcgatggt tacggtggcc tggtgacgac ggaccccgaaa | 60 |
| acggcagacc cggtgtatgg caaagttttt aacccgccgc gtaatctgct gccgggtcgc | 120 |
| ttcaccaacc tgctggatgt tgccgaagca tgcccgacgt ttctgcattt cgatggcgac | 180 |
| gtgccgtatg ttaccacgaa aaccgattcg gaccgtgtcc tggcccagtt tgacctgtcc | 240 |
| ctggcggcca agcatatgtc aaacaccttc ctggctggcc tggcgcagta ttacacccaa | 300 |
| tacagcggta cggtgaatct gcactttatg ttcaccggcc cgacggatgc taaagcgcgc | 360 |
| tatatgattg cctacgcacc gccgggtatg gaaccgccaa agaccccgga agcagctgcg | 420 |
| cattgcattc acgcggaatg ggacaccggc ctgaacagca atttacgtt ctctatcccg | 480 |
| tatctgagtg ccgcagatta tgcctacacc gcaagtgacg ctgcggaaac cacgaatgtc | 540 |
| cagggttggg tgtgtctgtt tcaaatcacg cacggcaagg ctgaaggtga tgcactggtt | 600 |
| gtgatggcgt cggcgggtaa agattttgaa ctgcgtctgc cggttgatgc ccgtcagcaa | 660 |

<210> SEQ ID NO 4
<211> LENGTH: 48
<212> TYPE: DNA
<213> ORGANISM: Artificial Sequence
<220> FEATURE:
<223> OTHER INFORMATION: Fully synthetic

<400> SEQUENCE: 4

| | |
|---|---|
| agcgtaaaac gtgggaccag tgtcggcatg aagccaagtc cacgccca | 48 |

<210> SEQ ID NO 5
<211> LENGTH: 45
<212> TYPE: DNA
<213> ORGANISM: Artificial Sequence

```
<220> FEATURE:
<223> OTHER INFORMATION: Fully synthetic

<400> SEQUENCE: 5
gacagcagcg aagaaaaatt tcttagaaga ataggaagat ttgga            45

<210> SEQ ID NO 6
<211> LENGTH: 69
<212> TYPE: DNA
<213> ORGANISM: Artificial Sequence
<220> FEATURE:
<223> OTHER INFORMATION: Fully synthetic

<400> SEQUENCE: 6
cgttggcgtc tggaaggcac cgatgataaa gaagaaccgg aaagccagcg tcgtattggc   60
cgttttggc                                                          69

<210> SEQ ID NO 7
<211> LENGTH: 681
<212> TYPE: DNA
<213> ORGANISM: Artificial Sequence
<220> FEATURE:
<223> OTHER INFORMATION: Fully synthetic

<400> SEQUENCE: 7
accacctcca taggtgagtc ggctgacccc gtgactgcca ctgttgagaa ctacggtggt   60
gagacacagg tccagagacg ccaacacacg gatgtctcgt tcatattaga cagatttgtg  120
aaagtaacac caaaagacca aattaatgtg ttggacctga tgcaaacccc tgcacacact  180
ttggtaggcg cgctcctccg tactgccacc tactacttcg cagatctaga agtggcagtg  240
aaacacgagg gaaaccttac ctgggtcccg aatggggcgc ccgaaacagc gttggacaac  300
accaccaatc aacggctta ccacaaggca ccgctcaccc ggcttgcact gccttacacg  360
gcaccacacc gtgtcttggc tactgtttac aacgggaact gcaagtatgg cgagagcccc  420
gtgaccaatg cgagaggtga cctgcaagta aaagcggcaa gagcgctgcc tacctcagcg  480
taaaacgtgg gaccagtgtc ggcatgaagc caagtccacg cccattggcc cagcttcaat  540
tacggtgcca tcaaagccac tcgggtgact gaactgcttt accgcatgag gagggccgaa  600
acatactgcc cccggcctct tttggctatt caccccgagcg aagctagaca caaacaaaag  660
attgtggcgc ctgtgaaaca g                                            681

<210> SEQ ID NO 8
<211> LENGTH: 678
<212> TYPE: DNA
<213> ORGANISM: Artificial Sequence
<220> FEATURE:
<223> OTHER INFORMATION: Fully synthetic

<400> SEQUENCE: 8
accacctcca taggtgagtc ggctgacccc gtgactgcca ctgttgagaa ctacggtggt   60
gagacacagg tccagagacg ccaacacacg gatgtctcgt tcatattaga cagatttgtg  120
aaagtaacac caaaagacca aattaatgtg ttggacctga tgcaaacccc tgcacacact  180
ttggtaggcg cgctcctccg tactgccacc tactacttcg cagatctaga agtggcagtg  240
aaacacgagg gaaaccttac ctgggtcccg aatggggcgc ccgaaacagc gttggacaac  300
accaccaatc aacggctta ccacaaggca ccgctcaccc ggcttgcact gccttacacg  360
gcaccacacc gtgtcttggc tactgtttac aacgggaact gcaagtatgg cgagagcccc  420
```

| | |
|---|---|
| gtgaccaatg cgagaggtga cctgcaagta aaagcggcaa gagcgctgcc tacctcgaca | 480 |
| gcagcgaaga aaaatttctt agaagaatag gaagatttgg attggcccag cttcaattac | 540 |
| ggtgccatca aagccactcg ggtgactgaa ctgctttacc gcatgaggag ggccgaaaca | 600 |
| tactgccccc ggcctctttt ggctattcac ccgagcgaag ctagacacaa acaaaagatt | 660 |
| gtggcgcctg tgaaacag | 678 |

<210> SEQ ID NO 9
<211> LENGTH: 702
<212> TYPE: DNA
<213> ORGANISM: Artificial Sequence
<220> FEATURE:
<223> OTHER INFORMATION: Fully synthetic

<400> SEQUENCE: 9

| | |
|---|---|
| accacctcca taggtgagtc ggctgacccc gtgactgcca ctgttgagaa ctacggtggt | 60 |
| gagacacagg tccagagacg ccaacacacg gatgtctcgt tcatattaga cagatttgtg | 120 |
| aaagtaacac caaaagacca aattaatgtg ttggacctga tgcaaccccc tgcacacact | 180 |
| ttggtaggcg cgctcctccg tactgccacc tactacttcg cagatctaga agtggcagtg | 240 |
| aaacacgagg gaaaccttac ctgggtcccg aatgggcgc ccgaaacagc gttggacaac | 300 |
| accaccaatc caacggctta ccacaaggca ccgctcaccc ggcttgcact gccttacacg | 360 |
| gcaccacacc gtgtcttggc tactgtttac aacgggaact gcaagtatgg cgagagcccc | 420 |
| gtgaccaatg cgagaggtga cctgcaagta aaagcggcaa gagcgctgcc tacctccgtt | 480 |
| ggcgtctgga aggcaccgat gataaagaag aaccggaaag ccagcgtcgt attggccgtt | 540 |
| ttggcttggc ccagcttcaa ttacggtgcc atcaaagcca ctcgggtgac tgaactgctt | 600 |
| taccgcatga ggagggccga acatactgc cccggcctc ttttggctat tcacccgagc | 660 |
| gaagctagac acaaacaaaa gattgtggcg cctgtgaaac ag | 702 |

<210> SEQ ID NO 10
<211> LENGTH: 51
<212> TYPE: DNA
<213> ORGANISM: Artificial Sequence
<220> FEATURE:
<223> OTHER INFORMATION: Fully synthetic

<400> SEQUENCE: 10

| | |
|---|---|
| gccatgggtc atcaccatca tcatcacggg tcggactcag aagtcaatca a | 51 |

<210> SEQ ID NO 11
<211> LENGTH: 44
<212> TYPE: DNA
<213> ORGANISM: Artificial Sequence
<220> FEATURE:
<223> OTHER INFORMATION: Fully synthetic

<400> SEQUENCE: 11

| | |
|---|---|
| ggatccgaga ccttaaggtc tcaacctcca atctgttcgc ggtg | 44 |

<210> SEQ ID NO 12
<211> LENGTH: 29
<212> TYPE: DNA
<213> ORGANISM: Artificial Sequence
<220> FEATURE:
<223> OTHER INFORMATION: Fully synthetic

<400> SEQUENCE: 12

| | |
|---|---|
| ggtctctagg taccaccagc acgggcgaa | 29 |

<210> SEQ ID NO 13
<211> LENGTH: 30
<212> TYPE: DNA
<213> ORGANISM: Artificial Sequence
<220> FEATURE:
<223> OTHER INFORMATION: Fully synthetic

<400> SEQUENCE: 13
cgcggatcct cacagacttt gtttgaccgg                              30

<210> SEQ ID NO 14
<211> LENGTH: 31
<212> TYPE: DNA
<213> ORGANISM: Artificial Sequence
<220> FEATURE:
<223> OTHER INFORMATION: Fully synthetic

<400> SEQUENCE: 14
ggtctctagg tggtgcgggc cagtcatctc c                            31

<210> SEQ ID NO 15
<211> LENGTH: 30
<212> TYPE: DNA
<213> ORGANISM: Artificial Sequence
<220> FEATURE:
<223> OTHER INFORMATION: Fully synthetic

<400> SEQUENCE: 15
cgcggatcct cattctttac tcggaaattc                              30

<210> SEQ ID NO 16
<211> LENGTH: 31
<212> TYPE: DNA
<213> ORGANISM: Artificial Sequence
<220> FEATURE:
<223> OTHER INFORMATION: Fully synthetic

<400> SEQUENCE: 16
ggtctctagg tggtatcttc ccggtggcgt g                            31

<210> SEQ ID NO 17
<211> LENGTH: 31
<212> TYPE: DNA
<213> ORGANISM: Artificial Sequence
<220> FEATURE:
<223> OTHER INFORMATION: Fully synthetic

<400> SEQUENCE: 17
cgcggatcct cattgctgac gggcatcaac c                            31

<210> SEQ ID NO 18
<211> LENGTH: 32
<212> TYPE: DNA
<213> ORGANISM: Artificial Sequence
<220> FEATURE:
<223> OTHER INFORMATION: Fully synthetic

<400> SEQUENCE: 18
gcaattggat cccgtccggc gtagaggatc ga                           32

<210> SEQ ID NO 19
<211> LENGTH: 33
<212> TYPE: DNA
<213> ORGANISM: Artificial Sequence
<220> FEATURE:

<223> OTHER INFORMATION: Fully synthetic

<400> SEQUENCE: 19
gcgcacctcg agtcacagag tctgtttctc agg  33

<210> SEQ ID NO 20
<211> LENGTH: 44
<212> TYPE: DNA
<213> ORGANISM: Artificial Sequence
<220> FEATURE:
<223> OTHER INFORMATION: Fully synthetic

<400> SEQUENCE: 20
ggcatgaagc caagtccacg cccattggcc cagaaagcgg caag  44

<210> SEQ ID NO 21
<211> LENGTH: 45
<212> TYPE: DNA
<213> ORGANISM: Artificial Sequence
<220> FEATURE:
<223> OTHER INFORMATION: Fully synthetic

<400> SEQUENCE: 21
gacactggtc ccacgtttta cgcttacttg caggtcacct ctcgc  45

<210> SEQ ID NO 22
<211> LENGTH: 41
<212> TYPE: DNA
<213> ORGANISM: Artificial Sequence
<220> FEATURE:
<223> OTHER INFORMATION: Fully synthetic

<400> SEQUENCE: 22
cgccgcattg gccgctttgg cttggcccag aaagcggcaa g  41

<210> SEQ ID NO 23
<211> LENGTH: 45
<212> TYPE: DNA
<213> ORGANISM: Artificial Sequence
<220> FEATURE:
<223> OTHER INFORMATION: Fully synthetic

<400> SEQUENCE: 23
aagaaatttt tcttcgctgc tgtctacttg caggtcacct ctcgc  45

<210> SEQ ID NO 24
<211> LENGTH: 57
<212> TYPE: DNA
<213> ORGANISM: Artificial Sequence
<220> FEATURE:
<223> OTHER INFORMATION: Fully synthetic

<400> SEQUENCE: 24
gaaccggaaa gccagcgtcg tattggccgt tttggcttgg cccagaaagc ggcaaga  57

<210> SEQ ID NO 25
<211> LENGTH: 56
<212> TYPE: DNA
<213> ORGANISM: Artificial Sequence
<220> FEATURE:
<223> OTHER INFORMATION: Fully synthetic

<400> SEQUENCE: 25
ttctttatca tcggtgcctt ccagacgcca acgtacttgc aggtcacctc tcgcat  56